United States Patent
Sato et al.

(10) Patent No.: US 6,395,739 B1
(45) Date of Patent: May 28, 2002

(54) N-PHENYL-N'-PHENYLPOPYLPIPERAZINE DERIVATIVES AND PROCESS FOR THE PREPARATION

(75) Inventors: Hiroki Sato; Eiichi Nagano; Jun Chikazawa; Mineo Takei; Raita Higashino, all of Konan-machi (JP)

(73) Assignee: Zeria Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/720,781

(22) PCT Filed: Jun. 28, 1999

(86) PCT No.: PCT/JP99/03448

§ 371 (c)(1),
(2), (4) Date: Dec. 29, 2000

(87) PCT Pub. No.: WO00/00471

PCT Pub. Date: Jan. 6, 2000

(30) Foreign Application Priority Data

Jun. 30, 1998 (JP) ............................................. 10-198148

(51) Int. Cl.[7] ..................... A61K 31/495; A61K 31/496; C07D 295/155; C07D 295/122; C07D 403/12
(52) U.S. Cl. ............................ 514/254.09; 514/255.03; 544/373; 544/394
(58) Field of Search ................................ 544/373, 394; 514/254.09, 255.03

(56) References Cited

U.S. PATENT DOCUMENTS 5,346,896 A * 9/1994 Ward et al. ................. 514/252
5,760,040 A * 6/1998 Yoshida et al. ............. 514/253

FOREIGN PATENT DOCUMENTS

EP 0 576 766 A1 1/1994
GB 1048903 11/1966

* cited by examiner

*Primary Examiner*—Emily Bernhardt
(74) *Attorney, Agent, or Firm*—Oblon, Spivak, McClelland, Maier & Neustadt, P.C.

(57) ABSTRACT

The present invention is directed to an N-phenyl-N'-phenylpropylpiperazine derivative represented by formula (1):

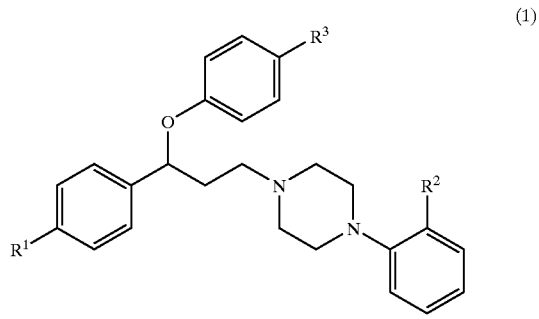

(wherein $R^1$ represents a lower alkyl group; $R^2$ represents a lower alkoxy group; and $R^3$ represents a cyano group, a carboxyl group, or an indolecarbonyl group); a medicament; and to a process for producing the derivative. The compound of the present invention is endowed with potent $\alpha_1$-adrenoceptor blocking activity, and thus is useful for the prevention or treatment of hypertension, congestive heart failure, myocardinal ischemia, arrhythmia, angina pectoris, and urinary obstruction and pollakiuria caused by benign prostatic hyperplasia.

52 Claims, No Drawings

N-PHENYL-N'-PHENYLPOPYLPIPERAZINE DERIVATIVES AND PROCESS FOR THE PREPARATION

TECHNICAL FIELD

The present invention relates to phenylpiperazine derivatives which have excellent $\alpha_1$-adrenoceptor blocking activity and are useful as medicaments; and to a process for producing the same.

BACKGROUND ART

A blocking agent against an $\alpha_1$-adrenoceptor, which dilates blood vessels or reduces resistance in the blood vessels, is known to be a preventive and therapeutic drug for hypertension such as essential hypertension or renal hypertension, congestive heart failure, myocardial ischemia, arrhythmia, and angina pectoris. Many compounds have been reported to serve as such a blocking agent. Moreover, an $\alpha_1$-adrenoceptor has been found to participate to a considerable degree in constriction of the urinary bladder neck (J. Urol., 134, 396 (1985)) and therefore, the blocking agent against the receptor has become of interest as a pharmaceutical capable of selectively treating urinary obstruction, pollakiuria, and other symptoms caused by benign prostatic hyperplasia (BPH). For example, prazosin hydrochloride and urapidil (British Patent No. 1156973, German Patent No. 1942405, WO89/12634, WO90/03972) have been used as pharmaceuticals for treatment of hypertension or urinary obstruction caused by BPH, and tamsulosin hydrochloride has been used as a pharmaceutical for treatment of urinary obstruction caused by BPH (Japanese Patent Application Laid-Open (Kokai) No. 110665/1981).

However, conventional blocking agents against an $\alpha_1$-adrenoreceptor do not necessarily exhibit sufficient effect for prevention and treatment of the above-described symptoms, and it is known that side effects such as orthostatic hypotension and loss of consciousness may result. In order to overcome these drawbacks, development of new drugs has still been demanded.

DISCLOSURE OF THE INVENTION

The present inventors have found that specific N-phenyl-N'-phenylpropylpiperazine derivatives exhibit excellent $\alpha_1$-adrenoreceptor blocking activity and thus are useful as medicaments. The present invention has been achieved on the basis of this finding.

Accordingly, the present invention provides an N-phenyl-N'-phenylpropylpiperazine derivative represented by formula (1):

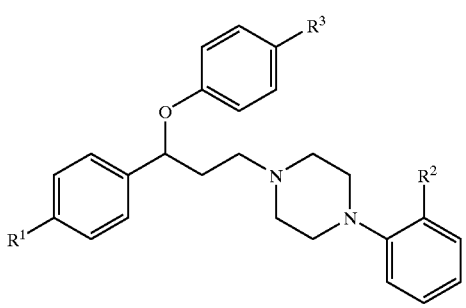

(1)

(wherein $R^1$ represents a lower alkyl group; $R^2$ represents a lower alkoxy group; and $R^3$ represents a cyano group, a carboxyl group, or an indolecarbonyl group) or a salt thereof, as well as a process for producing the derivative or the salt thereof.

The present invention also provides a medicament which comprises as an active component an N-phenyl-N'-phenylpropylpiperazine derivative represented by formula (1) or a salt thereof.

The present invention also provides a blocking agent against an $\alpha_1$-adrenoceptor, which blocking agent comprises as an active component an N-phenyl-N'-phenylpropylpiperazine derivative represented by formula (1) or a salt thereof.

Further, the present invention provides a pharmaceutical composition which contains an N-phenyl-N'-phenylpropylpiperazine derivative represented by formula (1) or a salt thereof and a pharmaceutically acceptable carrier.

Further, the present invention provides use of an N-phenyl-N'-phenylpropylpiperazine derivative represented by formula (1) or a salt thereof as medicaments.

Furthermore, the present invention provides a treatment method for hypertension, congestive heart failure, myocardinal ischemia, arrhythmia, angina pectoris, or urinary obstruction and pollakiuria caused by BPH, characterized by administration of an N-phenyl-N'-phenylpropylpiperazine derivative represented by formula (1) or a salt thereof.

WO95/26955 and WO99/03831, which have been filed by the present inventors, describe that an indole butyrate derivative has $\alpha_1$-adrenoceptor blocking activity, but are silent about the activity of the compound of formula (1).

BEST MODE FOR CARRYING OUT THE INVENTION

In the present invention, the term "lower" refers to the number of carbon atoms being 1 to 6 in a linear, branched, or cyclic carbon-containing group.

Accordingly, the term "a lower alkyl group" refers to a C1–C6 linear, branched, or cyclic alkyl group. Specific examples of such alkyl groups include methyl, ethyl, propyl, isopropyl, cyclopropyl, butyl, isobutyl, sec-butyl, tert-butyl, cyclobutyl, pentyl, 1-methylbutyl, 2-methylbutyl, isopentyl, tert-pentyl, 1,2-dimethylpropyl, neopentyl, 1-ethylpropyl, cyclopentyl, hexyl, 1-methylpentyl, 2-methylpentyl, 3-methylpentyl, isohexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methyl-1-ethylpropyl, 1-ethyl-2-methylpropyl, 1,1,2-trimethylpropyl, 1,2,2-trimethylpropyl, and cyclohexyl. Among these, C1–C4 linear or branched alkyl groups are preferred and a methyl group is most preferred.

The term "lower alkoxy group" refers to a C1–C6 linear, branched, or cyclic alkoxy group. Specific examples of such alkoxy groups include methoxy, ethoxy, propoxy, cyclopropoxy, isopropoxy, butoxy, isobutoxy, sec-butoxy, tert-butoxy, cyclobutoxy, pentyloxy, 1-methylbutoxy, 2-methylbutoxy, isopentyloxy, tert-pentyloxy, 1,2-dimethylpropoxy, neopentyloxy, 1-ethylpropoxy, cyclopentyloxy, hexyloxy, 1-methylpentyloxy, 2-methylpentyloxy, 3-methylpentyloxy, isohexyloxy, 1-ethylbutoxy, 2-ethylbutoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-methyl-1-ethylpropoxy, 1-ethyl-2-methylpropoxy, 1,1,2-trimethylpropoxy, 1,2,2-trimethylpropoxy, and cyclohexyloxy. Among these, C1–C4 linear or branched alkoxy groups are preferred and a methoxy group is most preferred.

In the present invention, the term "indolecarbonyl group" refers to a carbonyl group to which indole is bonded at one end. Specific examples of such indolecarbonyl groups include (indol-1-yl)carbonyl, (indol-2-yl)carbonyl, (indol-3-yl)carbonyl, (indol-4-yl)carbonyl, (indol-5-yl)carbonyl, (indol-6-yl)carbonyl, and (indol-7-yl)carbonyl. Among these, an (indol-3-yl)carbonyl group is most preferred.

In formula (1), $R^1$ is preferably a methyl group and $R^2$ is preferably a methoxy group. $R^3$ is preferably a cyano group, a carboxyl group, or an (indol-3-yl)carbonyl group and most preferably a cyano group or a carboxyl group.

The compound (1) of the present invention forms a salt with an acid or a base. Examples of salts formed with an acid include salts formed with mineral acids such as hydrochloric acid, hydrobromic acid, hydroiodic acid, sulfuric acid, nitric acid, and phosphoric acid; with organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; and with acidic amino acids such as aspartic acid and glutamic acid. Examples of salts formed with a base include salts formed with inorganic bases such as sodium, potassium, magnesium, calcium, aluminum, and zinc; and ammonium salts.

The present invention encompasses a variety of solvates or crystal polymorphisms of the compound (1) and further, encompasses racemic modifications and R- and S-stereoisomers as well as optically active substances of the compound (1).

The compound (1) of the present invention may be produced according to the following reaction scheme.

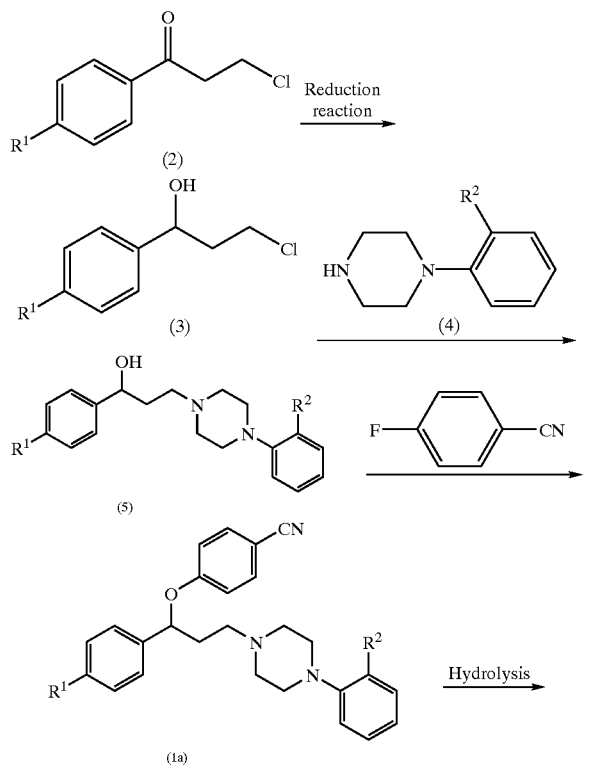

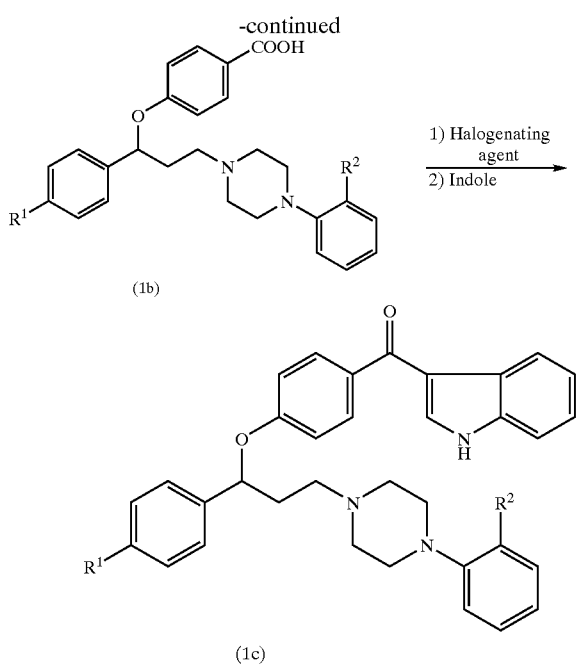

(wherein $R^1$ and $R^2$ are the same as described above.)

4'-Lower alkyl-3-chloropropiophenone (2) which has been prepared according to a known method is reduced by use of a borohydride such as sodium borohydride to thereby yield 3-chloro-1-(4-alkylphenyl)-1-propanol (3). The reaction may be carried out in an alcoholic solvent such as methanol or ethanol, under cooled conditions, at room temperature, under warm conditions, or with heat. The obtained 3-chloro-1-(4-alkylphenyl)-1-propanol (3) can be divided into isomers including a variety of optical isomers and R- and S-isomers by optical resolution using an optical resolving agent such as optically active mandelic acid, tartaric acid, dibenzoyltartaric acid, or di(p-toluoyl)tartaric acid.

When (R)-5,5-diphenyl-2-methyl-3,4-propano-1,3,2-oxazaborolidine and a borane-diethylaniline complex are added to compound (2) for reaction therebetween, an S-isomer of 3-chloro-1-(4-methylphenyl)-1-propanol (3) can be produced. Similarly, (S)-5,5-diphenyl-2-methyl-3,4-propano-1,3,2-oxazaborolidine and a borane-diethylaniline complex are added to compound (2), and the mixture is allowed to react to thereby obtain an R-isomer of 3-chloro-1-(4-methylphenyl)-1-propanol (3). By use of the R-isomer and the S-isomer in each of the following reactions, an R-isomer and an S-isomer of compound (1) of the present invention can be produced. In the above-described reduction, sodium borohydride, dimethyl sulfate, and N,N-diethylaniline can be added instead of a borane-diethylaniline complex.

When a 1-(2-lower alkoxyphenyl)piperazine derivative (4), potassium iodide, and a base are added to compound (3) and the mixture is allowed to react, N-(3-hydroxy-3-phenylpropyl)piperazine derivatives (5) can be produced. Examples of the base include metal carbonates such as potassium carbonate and sodium carbonate; trialkyl amines such as triethylamine and diisopropylethylamine; and pyridines such as pyridine, lutidine, and 4-dimethylaminopyridine. The reaction is usually carried out in a solvent which does not affect the reaction, such as N,N-dimethylformamide, dimethylsulfoxide, acetone, or methylene chloride. The reaction may be carried out at room temperature, under warm conditions, or with heat.

An N-(3-hydroxy-3-phenylpropyl)piperazine derivative (5) is reacted with p-fluorobenzonitrile to thereby obtain compound (1a) of the present invention in which $R^3$ is a cyano group. The reaction is usually carried out in the presence of a base such as sodium hydroxide, potassium hydroxide, potassium tert-butoxide, or sodium hydride; and in the presence or in the absence of a solvent which does not affect the reaction, such as N,N-dimethylformamide, dimethylsulfoxide, or tetrahydrofuran. The reaction may be carried out under cooled conditions, at room temperature, under warm conditions, or with heat.

Hydrolysis of the compound (1a) of the present invention in which $R^3$ is a cyano group provides compound (1b) of the present invention in which $R^3$ is a carboxylic group. The reaction is usually carried out in the presence of a base such as potassium hydroxide or sodium hydroxide and in a solvent such as methanol, ethanol, or tetrahydrofuran, or in a mixed solvent of one of the above solvent and water. The reaction is carried out under warm conditions, with heat, or under reflux with heat.

The compound (1b) of the present invention in which $R^3$ is a carboxylic group is reacted with a halogenating agent such as thionyl chloride, oxalyl chloride, phosphorus trichloride, or phosphorus pentachloride to thereby activate the carboxylic group of the compound (1b) and further, reacted with a separately-prepared reaction product between indole and an organometallic compound, to thereby obtain compound (1c) of the present invention in which $R^3$ is an indolecarbonyl group. The activation reaction of the carboxylic group of the compound (1b) may be carried out in the presence or in the absence of a solvent which does not affect the reaction, for example, a halogen-containing solvent such as methylene chloride and chloroform. The reaction may be carried out at room temperature, under warm conditions, or with heat. In the preparation of the reaction product between indole and an organometallic compound, there is employed a solvent which does not affect the reaction, for example, a halogen-containing solvent such as methylene chloride, chloroform, or 1,2-dichloroethane; ether such as diethyl ether, tetrahydrofuran, or dioxane; and benzene such as toluene or xylene. Examples of the organometallic compound include organic lithium compounds, organic aluminum compounds, organic zinc compounds, and organic magnesium compounds. Specific examples of organic lithium compounds include methyllithium and butyllithium; specific examples of organic aluminum compounds include trimethylaluminum and triethylaluminum; specific examples of organic zinc compounds include dimethylzinc and diethylzinc; and specific examples of organic magnesium compounds include methylmagnesium chloride, ethylmagnesium chloride, methylmagnesium bromide, ethylmagnesium bromide, methylmagnesium iodide, and ethylmagnesium iodide. The reaction may be carried out in the presence or in the absence of a zinc compound. Preferably, the reaction is carried out in the presence of a zinc compound and examples of the zinc compound include zinc chloride, zinc bromide, and zinc iodide. The reaction may be carried out under a cooled condition, at room temperature, under warm conditions, or with heat.

N-Phenyl-N'-phenylpropylpiperazine derivative (1) obtained in the present invention may be converted to a salt with an acid or a base according to a customary method.

N-Phenyl-N'-phenylpropylpiperazine derivative (1) and the salts thereof obtained in the present invention encompass a variety of solvates and crystal polymorphisms. Through suitable selection of raw materials, asymmetric reduction, and optical resolution using an optical resolving agent such as optically active mandelic acid, tartaric acid, dibenzoyltartaric acid, or di(p-toluoyl)tartaric acid, there can be produced different racemic modifications, a variety of optical isomers and R- and S-isomers.

The thus-obtained compound (1) of the present invention has excellent $\alpha_1$-adrenoceptor blocking activity and high safety. Therefore, the compound is useful as a preventive and therapeutic agent for hypertension, congestive heart failure, myocardinal ischemia, arrhythmia, angina pectoris, and urinary obstruction and pollakiuria caused by BPH.

The compound (1) of the present invention can be formed into a pharmaceutical composition for, for example, oral administration or parenteral administration, through formulation together with a pharmaceutically acceptable carrier. For oral administration, the compound (1) may be formed into tablets, powders, granules, or capsules through combination with suitable additives including excipients such as lactose, mannitol, corn starch, and crystalline cellulose; binders such as cellulose derivatives, gum arabic, and gelatin; disintegrators such as carboxymethylcellulose–Ca; and lubricants such as talc and magnesium stearate. The resultant solid preparations may be formed into enteric preparations by use of a coating agent such as hydroxypropylmethyl cellulose phthalate, hydroxypropylmethyl cellulose acetate succinate, cellulose acetate phthalate, or a methacrylate copolymer. For parenteral administration, the compound (1) may be formed into injection liquids through combination with, for example, water, ethanol, glycerin, and customary surfactants; or into suppositories through combination with a suppository base.

The dose may vary in accordance with age, body weight, symptom, therapeutic effect, manner of administration, and administration period. Generally, in the case of oral administration, compound (1) of the present invention is administered in an amount of 1–2000 mg/day, preferably 10–300 mg/day, at a single dose or 2–3 divided doses per day.

EXAMPLES

The present invention will next be described by way of examples, which should not be construed as limiting the invention thereto.

Example 1

Production of (S)-4-[3-[4-(2-methoxyphenyl)piperazin-1-yl]-1-(4-methylphenyl)propoxy]benzonitrile dihydrochloride (Step 1)

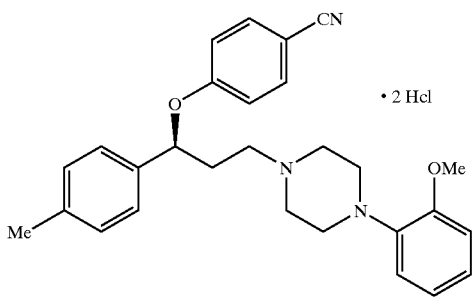

Production of 4'-methyl-3-chloropropiophenone

The target compound was produced according to a method described by A. A. Khalaf et al. (Bulletin de la Societe de France, N° 7–8, II 285–291, 1984).

Aluminum chloride (480 g) was suspended in methylene chloride (1125 mL). Nitromethane (195 mL) was added dropwise to the suspension and the resulting mixture was stirred for one hour at room temperature. Subsequently, toluene (321 mL) was added dropwise thereto and the mixture was stirred for one hour at room temperature. Further, to the mixture was added dropwise 3-chloropropionylchloride (289 mL) at 10–15° C. and the resultant mixture was stirred for 2 hours at room temperature. After the reaction mixture was cooled in an ice bath, ice, then methylene chloride, water, and concentrated hydrochloric acid were added to the mixture with stirring. The layers were separated, and the organic layer was washed sequentially with 1N hydrochloric acid, saturated sodium bicarbonate, and saturated brine, and dried over anhydrous sodium sulfate, after which the solvent was evaporated under reduced pressure. The residue was recrystallized from a solvent mixture of hexane and ethyl acetate, to thereby obtain 457.9 g of the target compound as white crystals.

Melting point: 77.5–78.5° C.

(Step 2)

Production of (S)-3-chloro-1-(4-methylphenyl)-1-propanol

4'-Methyl-3-chloropropiophenone (18.2 g) and (R)-5,5-diphenyl-2-methyl-3,4-propano-1,3,2-oxazabololidine (277 mg) were dissolved in tetrahydrofuran (100 mL) under argon atmosphere. Borane-diethylaniline complex (18 mL) was added dropwise to the solution with cooling with water and the resulting mixture was stirred for 1.5 hours at the same temperature. After the reaction mixture was cooled in an ice bath, methanol (50 mL) was added dropwise and the mixture was stirred for 30 minutes at the same temperature. 1N Hydrochloric acid was added thereto with stirring, and thereafter sodium chloride was added to the mixture for salting out, followed by extraction with ethyl acetate. After being washed with 1N hydrochloric acid, saturated sodium bicarbonate, and brine, the organic layer was dried over anhydrous sodium sulfate. The solvent was evaporated under reduced pressure, to thereby obtain 17.4 g of the target compound as a colorless solid.

Melting point: 48–50° C.

$^1$H-NMR (CDCl$_3$) δ: 1.90~1.94(1H,m), 2.00~2.13(1H, m), 2.16~2.30(1H, m). 3.50~3.60(1H, m), 3.67~3.78(1H, m), 4.90(1H, quint), 7.15~7.30(4H, m)

I R (KBr) cm$^{-1}$: 3300

MS (EI) m/e: 184,186 (M$^+$)

$[α]_D$ (C=1,CHCl$_3$): −22.5°

(Step 3)

Production of (S)-3-[4-(2-methoxyphenyl)piperazin-1-yl]-1-(4-methylphenyl)-1-propanol (S)-3-Chloro-1-(4-methylphenyl)-1-propanol (17.4 g), 1-(2-methoxyphenyl)piperazine hydrochloride (22.9 g), potassium iodide (49.8 g), and triethylamine (45 mL) were suspended in N,N-dimethylformamide (230 mL). The suspension was stirred for 16 hours at 60° C. The reaction mixture was poured into water. Saturated sodium bicarbonate was added thereto, followed by extraction with ethyl acetate. After the organic layer was washed with brine and dried over anhydrous sodium sulfate, the solvent was evaporated under reduced pressure. The residue was recrystallized from a solvent mixture of hexane and ethyl acetate, to thereby obtain 22.8 g of the target compound as light-pink crystals.

Melting point: 127.5–128.5° C.

$^1$H-NMR (CDCl$_3$) δ: 1.86~1.96(2H, m), 2.34(3H,s), 2.62~2.96(6H, m), 3.14(4H, br), 3.86(3H, s), 4.94(1H, t), 6.84~7.06(4H, m), 7.15(2H, d), 7.23~7.32(2H, m)

I R (KBr) cm$^{-1}$: 3400

MS (FAB) m/e: 341 (MH$^+$)

$[α]_D$ (C=1, CHCl$_3$): −60.8°

(Step 4)

Production of (S)-4-[3-[4-(2-methoxyphenyl)piperazin-1-yl]-1-(4-methylphenyl)propoxy]benzonitrile dihydrochloride (S)-3-[4-(2-Methoxyphenyl)piperazin-1-yl]-1-(4-methylphenyl)-1-propanol (22.7 g) and p-fluorobenzonitrile (8.88 g) were dissolved in N,N-dimethylformamide (230 mL). Potassium tert-butoxide (11.2 g) was added to the solution with cooling in an ice bath and the resulting mixture was stirred for 10 minutes at the same temperature. The reaction mixture was poured into water, and 1N hydrochloric acid was added thereto so as to adjust pH to 6, followed by extraction with ethyl acetate. After the organic layer was washed with brine and dried over anhydrous sodium sulfate, the solvent was evaporated under reduced pressure. The residue was dissolved in diethylether, and 4N hydrochloric acid-dioxane solution was added thereto, followed by concentration under reduced pressure. A mixed solvent of ethanol and diethylether was added to the residue with stirring, and thereafter, precipitated crystals were collected by filtration. The thus-collected crystals were washed with a mixed solvent of diethylether and ethyl acetate, to thereby obtain 32.5 g of the target compound as light-pink crystals (yield: 95%).

Melting point: 169.5–170.5° C. (decomposed)

$^1$H-NMR (CDCl$_3$) δ: 2.33(3H, s) 2.50~2.62(2H, m), 3.25~3.42(2H, m), 3.50~3.65(4H, m), 4.08(3H, s), 4.34~4.57(2H, m), 5.13(2H, t), 5.52(1H, t), 6.91(2H, d), 7.02~7.26(6H, m), 7.44~7.52(3H, m), 8.22(1H, dd), 13.90 (1H, brs)

I R (KBr) cm$^{-1}$: 3450, 3360, 2361, 2228, 1605

MS (FAB) m/e: 442 (MH$^+$)

$[α]_D$ (C=1, CHCl$_3$): 0.30°

Example 2

Production of (S)-4-[3-[4-(2-methoxyphenyl)piperazin-1-yl]-1-(4-methylphenyl)propoxy]benzoic acid

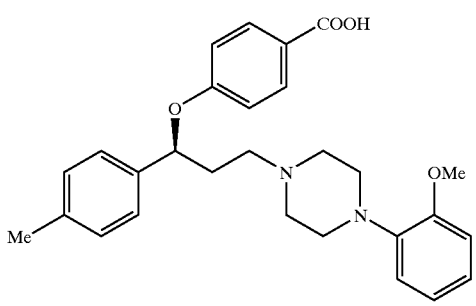

(S)-4-[3-[4-(2-Methoxyphenyl)piperazin-1-yl]-1-(4-methylphenyl)propoxy]benzonitrile dihydrochloride (32.0 g) was dissolved in 75% aqueous ethanol solution (320 mL) with heat. To the solution was added potassium hydroxide (81.9 g) and the mixture was refluxed for 20 hours. The reaction mixture was concentrated under reduced pressure. The residue was suspended in water, and concentrated hydrochloric acid was added thereto so as to adjust pH to 6. Subsequently, the mixture was extracted with methylene chloride. The organic layer was washed sequentially with saturated sodium bicarbonate and brine, and dried over anhydrous sodium sulfate. The solvent was evaporated under reduced pressure. Methanol was added to the residue to dissolve the residue with heat. The resultant mixture was then left to cool, to thereby obtain 24.5 g of the target compound as light-pink crystals (yield: 86%).

Melting point: 188–189° C. (decomposed)

$^1$H-NMR (CDCl$_3$) δ: 2.14~2.26(2H, m), 2.31(3H, s), 2.50~2.62(1H, m), 2.84~3.25(9H, m), 3.84(3H, s), 5.35(1H, t), 6.72(2H, d), 6.81~7.02(4H, m), 7.12(2H, d), 7.24(2H, d), 7.60(2H, d), 8.30(1H, br)

I R (KBr) cm$^{-1}$: 3450, 1655, 1603

MS (FAB) m/e: 461 (MH$^+$)

$[α]_D$ (C=1, CHCl$_3$): −35.0°

Example 3

Production of (S)-3-[4-[3-[4-(2-methoxyphenyl) piperazin-1-yl]-1-(4-methylphenyl)propoxy]benzoyl] indole hydrochloride

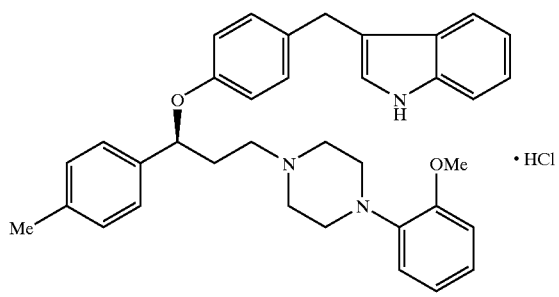

(S)-4-[3-[4-(2-Methoxyphenyl)piperazin-1-yl]-1-(4-methylphenyl)propoxy]benzoic acid (10.0 g) was added to methylene chloride (100 mL). Thionyl chloride (2 mL) was added to the solution, and the mixture was stirred for 10 minutes at room temperature. Methylene chloride and saturated sodium bicarbonate were added to the reaction mixture with stirring, after which the layers were separated. After the organic layer was washed with brine and dried over anhydrous magnesium sulfate, the solvent was evaporated under reduced pressure, to thereby obtain an acid chloride.

Independently, indole (3.06 g) was added to methylene chloride (30 mL). 3M Methylmagnesium bromide-diethylether solution (8.7 mL) was added to the solution with cooling in an ice bath, after which the resultant mixture was stirred for 10 minutes at the same temperature. Subsequently, 1M zinc chloride-diethylether (52.2 mL) was added thereto and the mixture was warmed to room temperature. The mixture was stirred for 20 minutes at room temperature. The previously obtained methylene chloride solution of acid chloride (100 mL) was added to the mixture for stirring for one hour at room temperature. After completion of reaction, methanol (50 mL) was added thereto with stirring, and thereafter, the mixture was poured into chloroform (200 mL). The mixture was washed sequentially with 1N hydrochloric acid, water, saturated sodium bicarbonate, and brine, and dried over anhydrous magnesium sulfate. The solvent was evaporated under reduced pressure. The residue was dissolved in a solvent mixture of ethyl acetate and methanol. 4N hydrochloric acid-dioxane was added to the resultant solution, and crystals so precipitated were collected by filtration, to thereby obtain 10.5 g of the target compound as light-pink crystals (yield: 81%).

Melting point: 163–166°C. (decomposed)

$^1$H-NMR (DMSO-d$_6$) δ: 2.20~2.60(5H, m), 3.08~3.67 (10H, m), 3.80(3H, s), 5.56~5.64(1H, m), 6.88~7.09(6H, m), 7.16~7.27(4H, m), 7.38(2H, d), 7.48~7.55(1H, m), 7.72(2H, d), 7.88(1H, d), 8.17~8.23(1H, m)

I R (KBr) cm$^{-1}$: 3320, 2290, 1609

MS (FAB) m/e: 560 (MH$^+$)

$[α]_D$ (C=1,MeOH): −15.4°

Separately, a suspension of (S)-3-[4-[3-[4-(2-methoxyphenyl)piperazin-1-yl]-1-(4-methylphenyl) propoxy]benzoyl]indole hydrochloride (2.0 g) in in methylene chloride was partitioned by addition of saturated sodium bicarbonate. The organic layer was washed with brine and dried over anhydrous magnesium sulfate, after which the solvent was evaporated under reduced pressure. The residue was recrystallized from a solvent mixture of ethyl acetate and diisopropyl ether, to thereby obtain 1.4 g of (S)-3-[4-[3-[4-(2-methoxyphenyl)piperazin-1-yl]-1-(4-methylphenyl)propoxy]benzoyl]indole as light-yellow crystals.

Melting point: 168~170° C.

$^1$H-NMR (CDCl$_3$) δ: 1.95~2.15(1H, m), 2.20~2.40(1H, m), 2.33(3H, s), 2.60(2H, brs), 2.68(4H, brs), 3.12(4H, brs), 3.86(3H, s), 5.33(1H, dd), 6.82~7.05(6H, m), 7.15(2H, d), 7.25~7.33(4H, m), 7.37~7.45(1H, m), 7.62(1H, d), 7.74(2H, d), 8.30~8.40(1H, m), 8.72(1H, brs)

I R (KBr) cm$^{-1}$: 1599

MS (FAB) m/e: 560 (MH$^+$)

$[α]_D^{20}$ (C=1.0, MeOH): −28.1°

<α$_1$-Adrenoceptor Blocking Activity>

Rabbits were exsanguinated to death, and the prostatic urethra and the prostate were removed and smooth muscle strips were prepared. Each strip was suspended in a 37° C. Krebs-solution-containing organ bath which had been bubbled with 95% O$_2$ and 5% CO$_2$. Isometric contraction under a resting tension of 1 g was recorded by an isometric transducer (by Nihon Koden: TB-651T) on a pen-type recorder (product of Nihon Denki San'ei: RECTI HORIZ 8K).

After the strips had been equilibrated for 60 minutes, contractions were elicited by use of a certain concentration of phenylephrine (10$^{-5}$ M). Subsequently, the organ bath was washed with a physiological solution, and the above procedure was repeated at 60-minute intervals of resting time until constant constriction responses of the strips were obtained. Next, phenylephrine was added cumulatively to organ bath(10$^{-7}$–3×10$^{-4}$ M), to thereby obtain concentration-response curves (control). After the resting period of 60 minutes following washing of the strip, test samples (DMSO solutions containing the test drug; 10$^{-7}$–10$^{-5}$ M) were treated for 30 minutes, and concentration-response curves of phenylephrine were obtained.

The composition of the physiological solution was as follows: NaCl 118.4 mM, KCl 4.7 mM, MgCl$_2$ 1.2 mM, CaCl$_2$ 2.5 mM, NaHCO$_3$ 25.0 mM, glucose 1.1 mM, and KH$_2$PO$_4$ 1.2 mM.

In all cases, 10$^{-5}$ M propranolol (β-adrenoceptor antagonist) was added to the physiological solution 10 minutes before test sample was treated with strip.

The potency of each test drug with regard to the α₁-adrenoceptor blocking activity was evaluated on the basis of calculation of pA₂ (inverse of the logarithm of the concentration by mole of the antagonist which, in the presence of the antagonist, requires twice the concentration of the agonist for providing the same effect as required in the absence of the antagonist). The results are shown in Table 1.

TABLE 1

|  | $pA_2$ | |
| --- | --- | --- |
|  | prostate | Urethra |
| Example 1 | 8.00 | 8.44 |
| Example 2 | 8.67 | 8.73 |
| Example 3 | 6.89 | 6.29 |

Formulation Example 1

The compound (20 g) of Example 1, lactose (315 g), cornstarch (125 g), and crystalline cellulose (25 g) were mixed homogeneously. A 7.5% aqueous solution (200 mL) of hydroxypropylcellulose was added thereto. The resultant mixture was granulated with an extruder equipped with a screen having a mesh of 0.5 mm. The thus-prepared granules were immediately rounded with a marumerizer and then dried, yielding a granular agent.

Formulation Example 2

By use of a fluidized granulator, granules prepared in Formulation Example 1 were coated with a film coating solution (1.9 kg) having the following composition, thereby yielding an enteric granular agent.

Composition of the coating solution: hydroxypropyl-methylcellulose phthalate (5.0%), stearic acid (0.25%), methylene chloride (50.0%), and ethanol (44.75%).

Formulation Example 3

The compound (20 g) of Example 2, lactose (100 g), corn starch (36 g), crystalline cellulose (30 g), carboxymethyl-cellulose calcium (10 g), and magnesium stearate (4 g) were mixed uniformly. The resultant mixture was formed into tablets, each weighing 200 mg, by use of a single-punch tableting machine which had a pestle of 7.5 mm in diameter.

Formulation Example 4

Tablets prepared in Formulation Example 3 were spray-coated with a coating solution having the following composition, thereby yielding enteric film-coated tablets, each coated with 10 mg of coating solution.

Composition of coating solution: hydroxypropyl-methylcellulose phthalate (8.0%), maibaset (0.4%), methylene chloride (50.0%), bleached beeswax (0.1%), and iso-propanol (41.5%).

Formulation Example 5

The compound (200 g) of Example 3, polysorbate 80 (20 g), and medium chain fatty acid triglyceride (1780 g) were mixed and dissolved completely. Subsequently, the resultant solution was formed into soft capsulated agents, each capsule containing 200 mg of the solution, by a rotary method using a soft capsulating liquid containing gelatin (100 parts), thick glycerin (30 parts), ethyl paraben (0.4 parts), and propyl paraben (0.2 parts).

Formulation Example 6

| Compound of Example 2 | 100 mg |
| --- | --- |
| Sodium acetate | 2 mg |
| Acetic acid (to adjust pH to 5.8) | Suitable amount |
| Distilled water | Balance |
| Total | 10 ml/vial |

The above ingredients were processed by a routine method to obtain an injection agent.

Industrial Applicability

The phenylpiperadine derivative of the present invention exhibits a potent α₁-adrenoceptor blocking action with high safety, and thus is useful for prevention and treatment of hypertension, congestive heart failure, myocardial ischemia, arrhythmia, angina pectoris, and in addition, urinary obstruction, pollakiuria, and other symptoms caused by BPH.

What is claimed is:

1. An N-phenyl-N'-phenylpropylpiperazine compound having the formula (1):

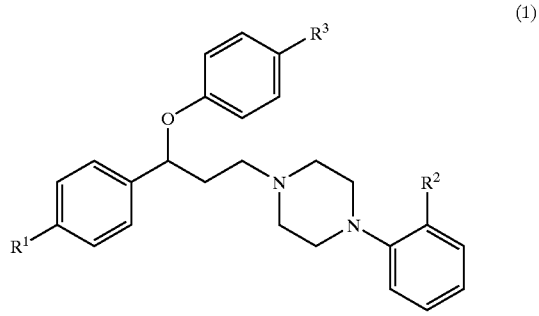

(1)

wherein $R^1$ is lower alkyl; $R^2$ is lower alkoxy; and $R^3$ is cyano, carboxyl, or indolecarbonyl; or a pharmaceutically-acceptable salt thereof; including crystal polymorphisms, R- or S-stereoisomers, or optically active isomers thereof.

2. The compound of claim 1, wherein $R^1$ is $C_1$–$C_4$ alkyl.

3. The compound of claim 2, wherein $R^1$ is methyl.

4. The compound of claim 1, wherein $R^2$ is $C_1$–$C_4$ alkoxy.

5. The compound of claim 4, wherein $R^2$ is methoxy.

6. The compound of claim 1, wherein $R^3$ is indolecarbonyl.

7. The compound of claim 6, wherein $R^3$ is (indol-3-yl)carbonyl.

8. The compound of claim 1, wherein $R^3$ is cyano.

9. The compound of claim 1, wherein $R^3$ is carboxyl.

10. The compound of claim 1, wherein $R^4$ is methyl, $R^2$ is methoxy and $R^3$ is carboxyl.

11. A pharmaceutical composition, comprising one or more of the compounds of claim 1, or a pharmaceutically acceptable salt or salts thereof; and a pharmaceutically-acceptable carrier.

12. The pharmaceutical composition of claim 11, which is in a single dosage form.

13. The pharmaceutical composition of claim 11, which is in a form suitable for oral or parenteral administration.

14. A method for treating hypertension, congestive heart failure, myocardial ischemia, arrhythmia, angina pectoris, urinary obstruction or pollakiuria caused by benign prostatic hyperplasia, or a combination thereof, which comprises administering an effective amount of one of more of the compounds of claim 1, or a pharmaceutically-acceptable salt or salts thereof to a mammal in need thereof.

15. The method of claim 14, wherein said mammal is a human.

16. A process for producing a compound of the formula (1a):

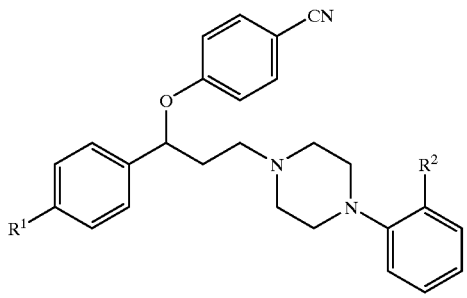

wherein $R^1$ is a lower alkyl, and $R^2$ is lower alkoxy, which comprises the step of reacting p-fluorobenzonitrile with a compound of the formula (5):

wherein $R^1$ and $R^2$ are as defined above.

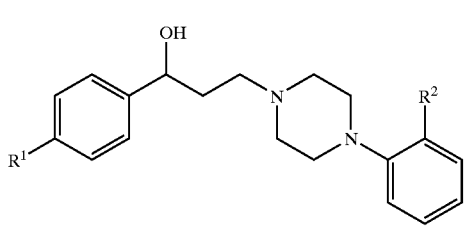

17. A process for producing a compound of the formula (1b):

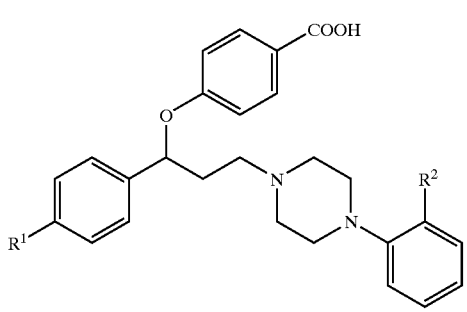

wherein $R^1$ is lower alkyl, and $R^2$ is lower alkoxy, which comprises the step of hydrolyzing a compound of formula (1a):

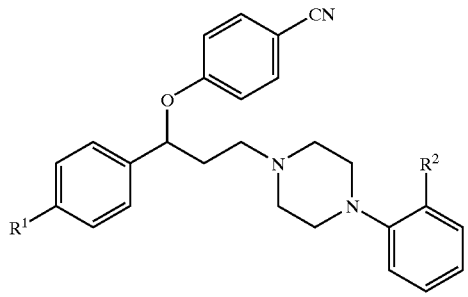

wherein $R^1$ and $R^2$ are as defined above.

18. A process for producing a compound of the formula (1c):

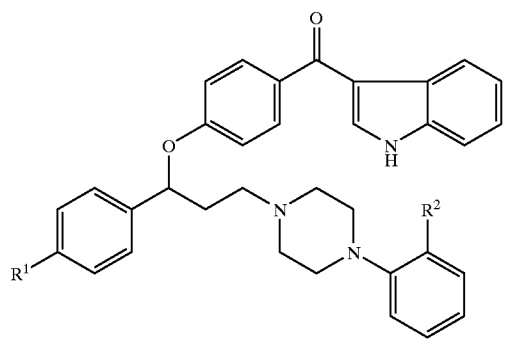

wherein $R^1$ is a lower alkyl, and $R^2$ is lower alkoxy, which comprises the steps of reacting a halogenating agent with a compound of the formula (1b):

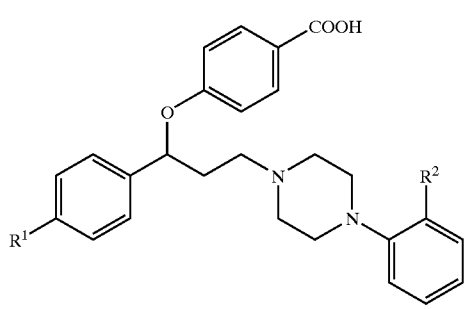

wherein $R^1$ and $R^2$ are as defined above, to form a product, and then reacting the product with a reaction product of indole and an organometallic compound optionally in the presence of a zinc compound.

19. A process for producing a compound of the formula (1b):

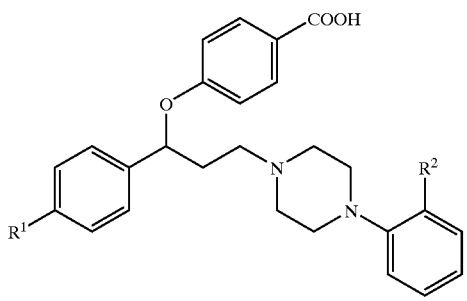
(1b)

wherein R¹ is lower alkyl, and R² is lower alkoxy, which comprises the steps of reacting p-fluorobenzonitrile with a compound of the formula (5):

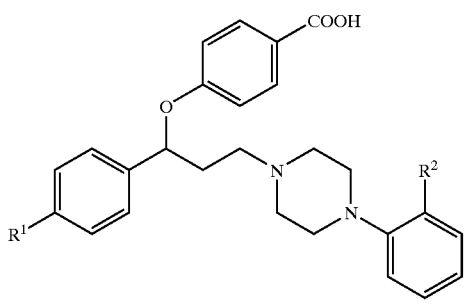
(5)

wherein R¹ and R² are as defined above, to thereby obtain a compound of the formula (1a):

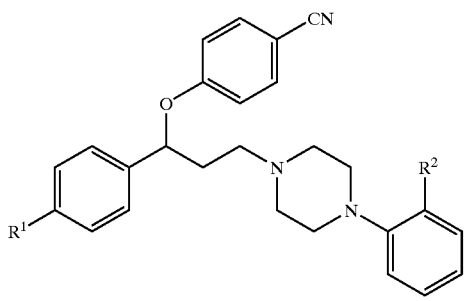
(1a)

wherein R¹ and R² are as defined above, and then hydrolyzing the compound (1a).

20. A process for producing a compound of the formula (1c):

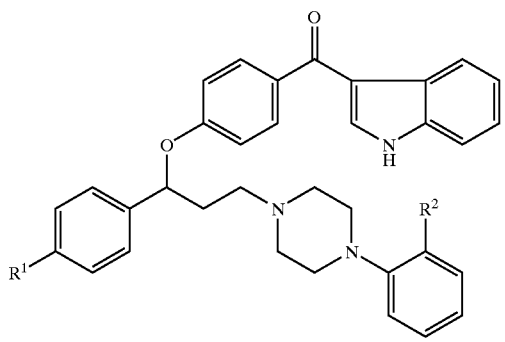
(1c)

wherein R¹ is lower alkyl, and R² is lower alkoxy, which comprises the steps of reacting p-fluorobenzonitrile with a compound of the formula (5):

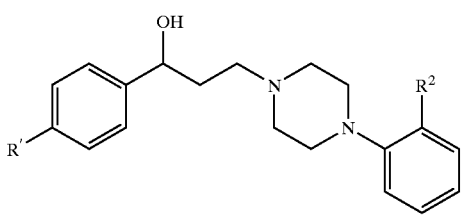
(5)

wherein R¹ and R² are as defined above, to thereby obtain a compound having the formula (1a):

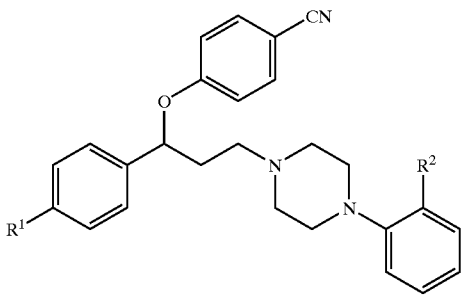
(1a)

wherein R¹ and R² are as defined above, and then hydrolyzing the compound (1a), to thereby obtain a compound having the formula (1b):

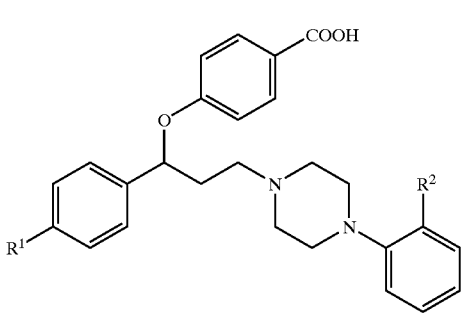
(1b)

wherein R¹ and R² are as defined above, and then reacting the compound having the formula (1b) with a reaction product of indole and an organometallic compound optionally in the presence of a zinc compound.

21. The process of claim 16, which is conducted in the presence of a base.

22. The process of claim 16, which is conducted in the presence of a solvent comprising N,N-dimethylformamide, dimethylsulfoxide or tetrahydrofuran.

23. The process of claim 21, wherein said base comprises sodium hydroxide, potassium hydroxide, potassium tert-butoxide or sodium hydride.

24. The process of claim 17, which is conducted in the presence of a base.

25. The process of claim 24, wherein said base comprises potassium hydroxide or sodium hydroxide.

26. The process of claim 17, which is conducted in the presence of a solvent.

27. The process of claim 26, wherein said solvent is methanol, ethanol or tetrahydrofuran.

28. The process of claim 26, which is conducted under solvent reflux.

29. The process of claim 18, wherein said halogenating agent is thionyl chloride, oxalyl chloride, phosphorus trichloride or phosphorus pentachloride.

30. The process of claim 18, wherein said reaction of said compound of the formula (1b) with said halogenating agent is conducted in the presence of a solvent, which is methylene chloride or chloroform.

31. The process of claim 30, wherein said solvent is methylene chloride, chloroform, 1,2-dichloroethane, diethyl ether, tetrahydrofuran, dioxane, benzene, toluene or xylene.

32. The process of claim 18, wherein said organometallic compound is organo-lithium compounds, organo-aluminum compounds, organo-zinc compounds or organo-magnesium compounds.

33. The process of claim 32, wherein said organometallic compound is an organo-lithium compound, which is methyllithium or butyllithium.

34. The process of claim 32, wherein said organometallic compound is an organo-aluminum compound, which is trimethylaluminum or triethylaluminum.

35. The process of claim 32, wherein said organometallic compound is an organo-zinc compound, which is dimethyl zinc or diethyl zinc.

36. The process of claim 32, wherein said organometallic compound is an organo-magnesium compound, which is methylmagnesium chloride, ethylmagnesium chloride, methylmagnesium bromide, ethylmagnesium bromide, methylmagnesium iodide or ethylmagnesium iodide.

37. The process of claim 18, wherein the reaction between said indole and said organometallic compound is conducted in the presence of a zinc compound.

38. The process of claim 37, wherein said zinc compound is zinc chloride, zinc bromide or zinc iodide.

39. The process of claim 19, wherein said reaction of said p-fluorobenzonitrile with said compound of the formula (5) is conducted in the presence of a solvent which is N,N-dimethyl formamide, dimethyl sulfoxide or tetrahydrofuran.

40. The process of claim 19, wherein said reaction of said p-fluorobenzonitrile with said compound of the formula (5) is conducted in the presence of a base.

41. The process of claim 19, wherein said hydrolysis of the compound (1a) is effected in the presence of a base and a solvent, said solvent being under reflux.

42. The process of claim 20, wherein said reaction of said p-fluorobenzonitrile with said compound of the formula (5) is conducted in the presence of a solvent which is N,N-dimethyl formamide, dimethyl sulfoxide or tetrahydrofuran.

43. The process of claim 20, wherein said reaction of said p-fluorobenzonitrile with said compound of the formula (5) is conducted in the presence of a base.

44. The process of claim 20, wherein said hydrolysis of the compound (1a) is effected in the presence of a base and a solvent, said solvent being under reflux.

45. The process of claim 44, wherein said solvent is methylene chloride, chloroform, 1,2-dichloroethane, diethyl ether, tetrahydrofuran, dioxane, benzene, toluene or xylene.

46. The process of claim 20, wherein said organometallic compound is organo-lithium compounds, organo-aluminum compounds, organo-zinc compounds or organo-magnesium compounds.

47. A method for treating urinary obstruction or pollakiuria caused by benign prostatic hyperplasia, which comprises the step of administering to a mammal in need thereof, an effective amount of one or more of the compounds of claim 1, or a pharmaceutically acceptable salt or salts thereof.

48. The method of claim 47, wherein said mammal is a human.

49. A method for treating hypertension, congestive heart failure, myocardial ischemia, arrythmia or angina pectoris, which comprises the step of administering to a mammal in need thereof, an effective amount of one or more of the compounds of claim 1, or a pharmaceutically acceptable salt or salts thereof.

50. The method of claim 49, wherein said mammal is a human.

51. A method of treating symptoms caused by benign prostatic hyperplasia in a mammal, which comprises administering to said mammal an effective amount of one or more of the compounds of claim 1, or a pharmaceutically acceptable salt or salts thereof.

52. The method of claim 51, wherein said mammal is a human.

* * * * *

UNITED STATES PATENT AND TRADEMARK OFFICE
CERTIFICATE OF CORRECTION

PATENT NO. : 6,395,739 B1
DATED : May 28, 2002
INVENTOR(S) : Sato et al.

It is certified that error appears in the above-identified patent and that said Letters Patent is hereby corrected as shown below:

<u>Title page, Item [54] and Column 1, lines 1-3,</u>
Title should read -- [54] N-PHENYL-N'-PHENYLPROPYLPIPERAZINE DERIVATIVES AND PROCESS FOR THE PREPARATION THEREOF --

Signed and Sealed this

Eighth Day of October, 2002

*Attest:*

*Attesting Officer*

JAMES E. ROGAN
*Director of the United States Patent and Trademark Office*